United States Patent
Zhang et al.

(10) Patent No.: US 9,775,559 B2
(45) Date of Patent: Oct. 3, 2017

(54) STAGED RHYTHM DETECTION SYSTEM AND METHOD

(71) Applicant: Medtronic, Inc., Minneapolis, MN (US)

(72) Inventors: Xusheng Zhang, Shoreview, MN (US); Mark L Brown, North Oaks, MN (US); Saul E Greenhut, Aurora, CO (US); Robert W Stadler, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 303 days.

(21) Appl. No.: 14/253,408

(22) Filed: Apr. 15, 2014

(65) Prior Publication Data
US 2014/0323894 A1   Oct. 30, 2014

Related U.S. Application Data

(60) Provisional application No. 61/816,345, filed on Apr. 26, 2013.

(51) Int. Cl.
*A61B 5/00* (2006.01)
*A61B 5/04* (2006.01)
(Continued)

(52) U.S. Cl.
CPC ........ *A61B 5/4836* (2013.01); *A61B 5/04012* (2013.01); *A61B 5/0464* (2013.01); *A61B 5/7246* (2013.01); *A61N 1/3621* (2013.01); *A61N 1/3702* (2013.01); *A61N 1/37264* (2013.01); *A61N 1/37282* (2013.01); *A61N 1/385* (2013.01); *A61N 1/39* (2013.01)

(58) Field of Classification Search
CPC .......................... A61B 5/4836; A61B 5/04012
USPC .............................................. 600/518; 607/28
See application file for complete search history.

(56) References Cited

U.S. PATENT DOCUMENTS

| 4,680,708 A | 7/1987 | Ambos |
| 4,870,974 A | 10/1989 | Wang |

(Continued)

FOREIGN PATENT DOCUMENTS

EP   046695 A2   1/1992

OTHER PUBLICATIONS (PCT/US2014/035100) PCT Notification of Transmittal of the International Search Report and the Written Opinion of the International Searching Authority.

*Primary Examiner* — Nadia A Mahmood

(57) ABSTRACT

A medical device and associated method for detecting and treating tachyarrhythmias acquires a cardiac signal using electrodes coupled to a sensing module. During an initial detection process, a shockable cardiac rhythm is detected by a processing module configured to compare the cardiac signal to a first set of detection criteria. By analyzing the cardiac signal, the processing module establishes at least one patient-specific detection threshold during the initial detection process. Upon establishing the at least one patient-specific detection threshold, the initial detection process is stopped, and a next detection process is started which includes comparing the cardiac signal to a second set of detection criteria including the at least one patient-specific detection threshold. In some embodiments, user programming of tachyarrhythmia detection parameters is not required.

41 Claims, 7 Drawing Sheets

(51) Int. Cl.
- *A61B 5/0464* (2006.01)
- *A61N 1/37* (2006.01)
- *A61N 1/38* (2006.01)
- *A61N 1/372* (2006.01)
- *A61N 1/362* (2006.01)
- *A61N 1/39* (2006.01)

(56) References Cited

U.S. PATENT DOCUMENTS

| | | |
|---|---|---|
| 5,191,884 A | 3/1993 | Gilli et al. |
| 5,273,049 A | 12/1993 | Steinhaus et al. |
| 5,280,792 A | 1/1994 | Leong et al. |
| 5,312,443 A | 5/1994 | Adams et al. |
| 5,334,966 A | 8/1994 | Takeshima et al. |
| 5,687,733 A | 11/1997 | McKown |
| 5,720,295 A | 2/1998 | Greenhut et al. |
| 6,134,479 A | 10/2000 | Brewer et al. |
| 6,230,059 B1 | 5/2001 | Duffin |
| 6,287,328 B1 | 9/2001 | Snyder et al. |
| 6,304,773 B1 | 10/2001 | Taylor et al. |
| 6,393,316 B1 | 5/2002 | Gillberg |
| 6,397,100 B2 | 5/2002 | Stadler et al. |
| 6,449,503 B1 | 9/2002 | Hsu |
| 6,526,313 B2 | 2/2003 | Sweeney |
| 6,892,094 B2 | 5/2005 | Ousdigian et al. |
| 7,010,347 B2 | 3/2006 | Schecter |
| 7,076,289 B2 | 7/2006 | Sarkar |
| 7,103,464 B2 | 9/2006 | Zielke |
| 7,200,435 B2 | 4/2007 | Ricci |
| 7,474,916 B2 | 1/2009 | Gutierrez |
| 7,734,333 B2 | 6/2010 | Ghanem et al. |
| 7,734,336 B2 | 6/2010 | Ghanem et al. |
| 7,742,812 B2 | 6/2010 | Ghanem et al. |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,774,616 B2 | 8/2010 | Dale et al. |
| 7,904,153 B2 | 3/2011 | Greenhut et al. |
| 7,907,993 B2 | 3/2011 | Ghanem et al. |
| 7,908,001 B2 | 3/2011 | Li et al. |
| 7,930,020 B2 | 4/2011 | Zhang |
| 7,937,135 B2 | 5/2011 | Ghanem et al. |
| 7,941,214 B2 | 5/2011 | Kleckner et al. |
| 7,991,459 B2 | 8/2011 | Palreddy |
| 7,991,471 B2 | 8/2011 | Ghanem et al. |
| 8,068,901 B2 | 11/2011 | Ghanem et al. |
| 8,095,206 B2 | 1/2012 | Ghanem et al. |
| 8,145,301 B2 | 3/2012 | Kim |
| 8,160,684 B2 | 4/2012 | Ghanem et al. |
| 8,306,618 B2 | 11/2012 | Ghanem et al. |
| 8,315,699 B2 | 11/2012 | Stadler |
| 8,435,185 B2 | 5/2013 | Ghanem et al. |
| 2002/0058878 A1 | 5/2002 | Kohler et al. |
| 2002/0165459 A1 | 11/2002 | Starobin et al. |
| 2003/0083587 A1 | 5/2003 | Ferek-Petric |
| 2003/0120312 A1 | 6/2003 | Cammilli et al. |
| 2004/0021523 A1 | 2/2004 | Sadowy et al. |
| 2004/0030256 A1 | 2/2004 | Lin |
| 2004/0049120 A1 | 3/2004 | Cao et al. |
| 2004/0059237 A1 | 3/2004 | Narayan et al. |
| 2004/0093037 A1 | 5/2004 | Henry |
| 2004/0254613 A1 | 12/2004 | Ostroff et al. |
| 2006/0042809 A1 | 3/2006 | Neufeld et al. |
| 2006/0116592 A1 | 6/2006 | Zhou |
| 2006/0217621 A1 | 9/2006 | Kim et al. |
| 2007/0232948 A1* | 10/2007 | Stadler .................. A61B 5/046 600/512 |
| 2007/0233198 A1 | 10/2007 | Ghanem et al. |
| 2007/0270704 A1 | 11/2007 | Ghanem et al. |
| 2009/0287268 A1 | 11/2009 | Nabutovsky et al. |
| 2012/0095520 A1* | 4/2012 | Zhang .................. A61B 5/0422 607/15 |
| 2013/0030481 A1 | 1/2013 | Ghosh |

\* cited by examiner

STAGED RHYTHM DETECTION SYSTEM AND METHOD

CROSS-REFERENCE TO RELATED APPLICATIONS

This application claims the benefit of U.S. Provisional Application No. 61/816,345, filed on Apr. 26, 2013. The disclosure of the above application is incorporated herein by reference in its entirety.

TECHNICAL FIELD

The disclosure relates generally to implantable medical devices and, in particular, to an apparatus and method for tachyarrhythmia detection and discrimination.

BACKGROUND

Implantable medical devices are available for treating cardiac arrhythmias by delivering anti-tachycardia pacing therapies and electrical shock therapies for cardioverting or defibrillating the heart. Such a device, commonly known as an implantable cardioverter defibrillator or "ICD", conventionally senses a cardiac signal to determine a patient's heart rate and classifies the rate according to a number of heart rate zones in order to detect episodes of ventricular tachycardia (VT) or ventricular fibrillation (VF). A number of rate zones may be defined according to programmable detection interval ranges for detecting slow ventricular tachycardia, fast ventricular tachycardia and ventricular fibrillation. Intervals between sensed R-waves, corresponding to the depolarization of the ventricles, are measured. Sensed R-R intervals falling into programmable detection interval ranges are counted to provide a count of VT or VF intervals. A programmable number of intervals to detect (NID) define the number of tachycardia intervals occurring consecutively or out of a given number of preceding event intervals that are required to detect VT or VF.

In some ICDs, tachyarrhythmia detection may begin with detecting a fast ventricular rate, referred to as a rate- or interval-based detection. Once VT or VF is detected based on rate, the morphology of the sensed depolarization signals may be analyzed to discriminate between heart rhythms to improve the sensitivity and specificity of tachyarrhythmia detection methods and therapy decision-making. For example, before a therapy decision is made, tachyarrhythmia detection may require discrimination between supraventricular tachycardia (SVT) and VT using cardiac signal waveform morphology analysis or other higher level cardiac signal analysis, particularly when a fast 1:1 atrial to ventricular rate is being sensed.

Programmable parameters for controlling the detection process may set various thresholds, boundaries, or other detection criteria to be applied to RR intervals and cardiac signal morphology for detecting and discriminating SVT, VT and VF. With the advancement of tachyarrhythmia detection methods, numerous features of an intracardiac electrogram (EGM) or ECG signal may be analyzed to enhance the sensitivity and specificity of tachyarrhythmia detection. The burden on the clinician in programming an ICD is increased with an increasing number of features to be analyzed and corresponding detection thresholds to be programmed. In some ICDs, upwards of hundreds of parameters controlling ICD function may be programmable. The complexity and sheer number of programmable parameters may lead to programming error, potentially resulting in unneeded therapies being delivered or a lack of therapy when it is needed. The programming burden placed on a clinician or technical support staff is considerable. The availability of ICDs to patients in some geographical regions may be limited due to a lack of local technical expertise required in programming the device. A need remains, therefore, for ICD systems that address and alleviate the burden and complexity of programming ICD control parameters.

DETAILED DESCRIPTION

An IMD, or other device, according to the present disclosure includes a cardiac signal analysis module for detecting and discriminating tachyarrhythmia in a patient. The cardiac signal analysis module operates to perform an evolving, staged rhythm detection process in which a first rhythm detection process operates initially to detect rhythms using population-based detection thresholds. This first rhythm detection process provides a safety mode for detecting treatable tachycardia while simultaneously learning patient-specific signal features for establishing patient-specific detection thresholds. Once a required set of patient-specific signal features are determined and verified, the operation of the cardiac signal analysis module switches to a second rhythm detection process that utilizes the patient-specific criteria and updates these criteria in an on-going, evolving process. In some embodiments, the second detection process performs a different detection algorithm than the first detection process in that the second detection process utilizes new criteria that requires determination of cardiac signal features and the use of patient-specific thresholds determined during the learning process that were unavailable during the initial first detection process.

Figure 1:
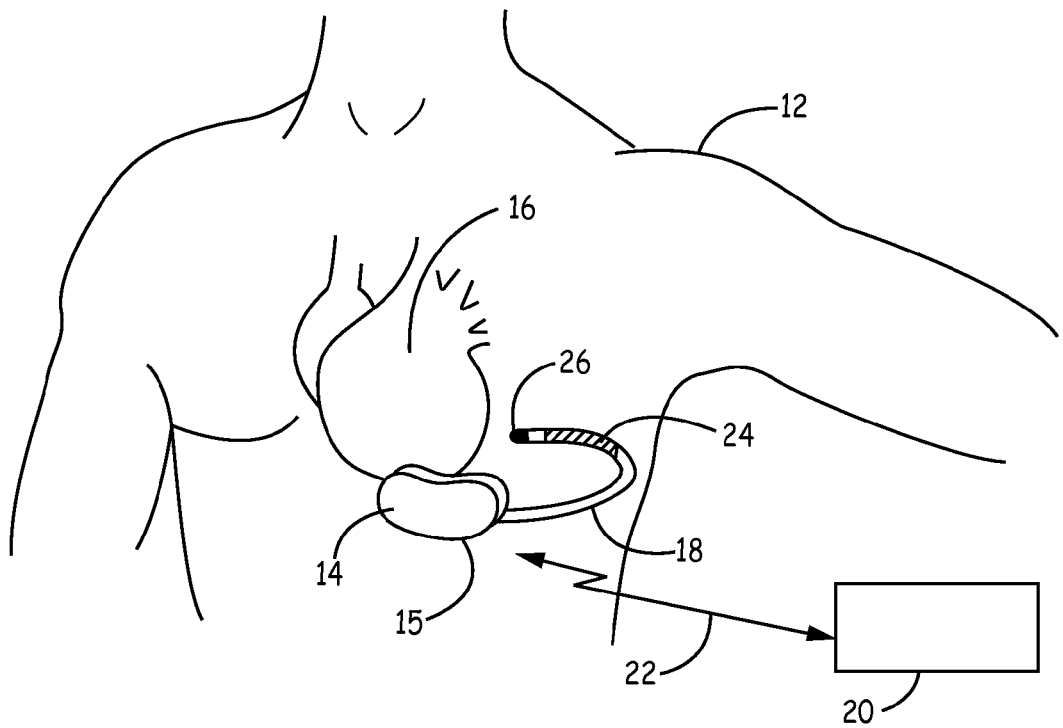
FIG. 1 and FIG. 2 are schematic diagrams of an implantable medical device (IMD) in which methods described herein may be usefully practiced.
Figure 2:
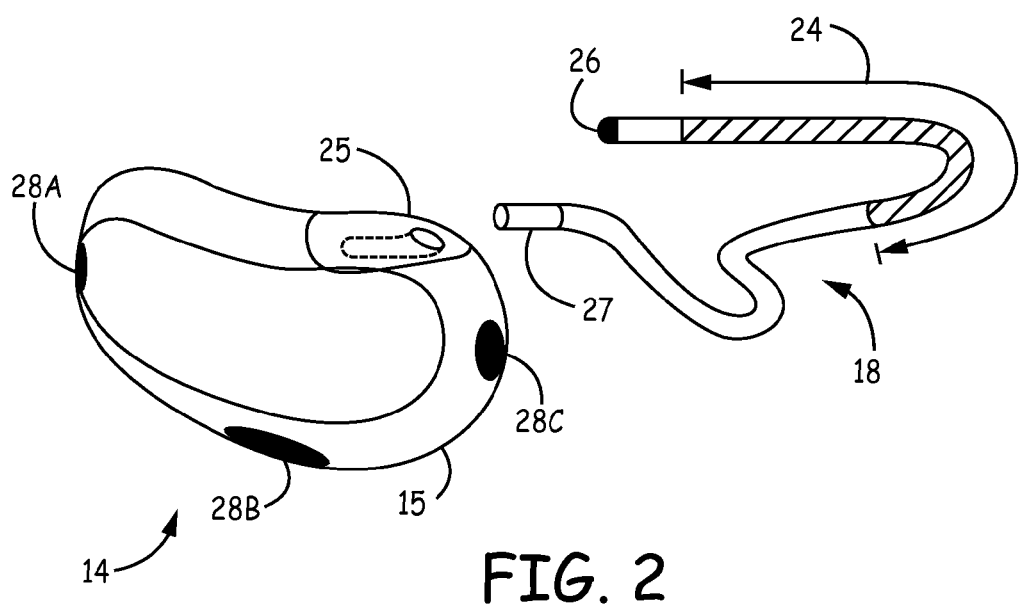

FIG. 1 and FIG. 2 are schematic diagrams of an IMD 14 in which methods described herein may be usefully practiced. As illustrated in FIG. 1, IMD 14 according to one embodiment is subcutaneously implanted outside the ribcage of a patient 12, anterior to the cardiac notch. IMD 14 includes a housing 15 to enclose electronic circuitry of the device 14.

In the example shown, sensing and cardioversion/defibrillation therapy delivery lead 18 in electrical communication with IMD 14 is tunneled subcutaneously into a location adjacent to a portion of a latissimus dorsi muscle of patient 12. Specifically, lead 18 is tunneled subcutaneously from a median implant pocket of IMD 14 laterally and posteriorly to the patient's back to a location opposite the heart such that the heart 16 is disposed between IMD 14 and a distal coil electrode 24 and a distal sensing electrode 26 of lead 18. Other lead configurations and implant positions may be used.

Subcutaneous lead 18 includes a distal defibrillation coil electrode 24, a distal sensing electrode 26, an insulated flexible lead body and a proximal connector pin 27 (shown in FIG. 2) for connection to subcutaneous device 14 via a connector 25. In addition, one or more electrodes 28A, 28B, 28C, collectively 28, (shown in FIG. 2) are positioned along the outer surface of the housing to form a housing-based subcutaneous electrode array (SEA). Distal sensing electrode 26 is sized appropriately to match the sensing impedance of the housing-based subcutaneous electrode array. It is understood that while IMD 14 is shown with electrodes 28 positioned on housing 15, electrodes 28 may be alternatively positioned along one or more separate leads connected to device 14 via connector 25.

The lead and electrode configuration shown in FIG. 1 is merely illustrative of one arrangement of electrodes that can be used for sensing subcutaneous ECG signals and delivering cardioversion/defibrillation shocks. Numerous configurations may be implemented that include one or more housing-based electrodes and/or one or more lead-based electrodes for enabling sensing of an ECG signal along one or more sensing vectors using extra-vascular, extra-cardiac electrodes implanted beneath the skin, muscle or other tissue layer within a patient's body, within or outside the thoracic cavity.

The tachyarrhythmia detection techniques disclosed herein are useful in an IMD system utilizing subcutaneous ECG sensing electrodes. A subcutaneous IMD system is less invasive and more easily implanted than a system including transvenous or epicardial leads. However, the techniques disclosed herein may be implemented in any ICD system, which may include any combination of intracardiac, epicardial, subcutaneous, lead-based and/or housing based electrodes for sensing ECG and/or intracardiac electrogram (EGM) signals. The description of tachyarrhythmia detection methods presented herein refers primarily to analysis of subcutaneous ECG signals for the sake of illustration, but it is contemplated that in other embodiments EGM signals or a combination of ECG (subcutaneous or surface) and EGM signals might be used for tachyarrhythmia detection and discrimination by a medical device configured to detect tachyarrhythmia and delivery tachyarrhythmia therapies. The tachyarrhythmia detection processes described herein which reduce the burden of programming detection parameters in an ICD may be implemented in any device and lead/electrode configuration capable of detecting and treating tachyarrhythmia.

Further referring to FIG. 1, a programmer 20 is shown in telemetric communication with IMD 14 by an RF communication link 22. Communication link 22 may be any appropriate RF link such as Bluetooth, WiFi, or Medical Implant Communication Service (MICS). Programmer 20 is used to retrieve data from IMD 14 and to program operating parameters and programs in IMD 14 for controlling IMD 14 functions. For example, programmer 20 may be used to program therapy control parameters, however, the techniques disclosed herein are intended to minimize the number of parameters and time required for a clinician or technician to program the IMD 14, particularly tachyarrhythmia detection parameters. Programmer 20 may be used to retrieve data acquired by IMD 14. Retrieved data may be reviewed by a clinician for verification or "truthing" of detected tachyarrhythmia episodes. For example, an expert may review ECG signal samples recorded and stored by IMD 14 and confirm a classification of the rhythm made by IMD 14 or input a new classification. A classification may be SVT, VT, or VF or sub-classifications thereof. Truthed episode data may be returned to the IMD 14 for use in setting patient-specific detection thresholds as further described below. A clinician may retrieve and review other data from IMD 14 using programmer 20, such as retrieving automatically set patient-specific detection thresholds, morphology template, and ECG signal recordings during various heart rates and rhythms obtained by the IMD 14.

IMD 14 and associated lead 18 are referred to as a "subcutaneous IMD system" because lead 18 is positioned in an extravascular location, subcutaneously. It is understood that while IMD 14 and lead 18 may be positioned between the skin and muscle layer of the patient, IMD 14 and any associated leads could be positioned in any extravascular location of the patient, such as below the muscle layer or within the thoracic cavity, for example.

Figure 3:
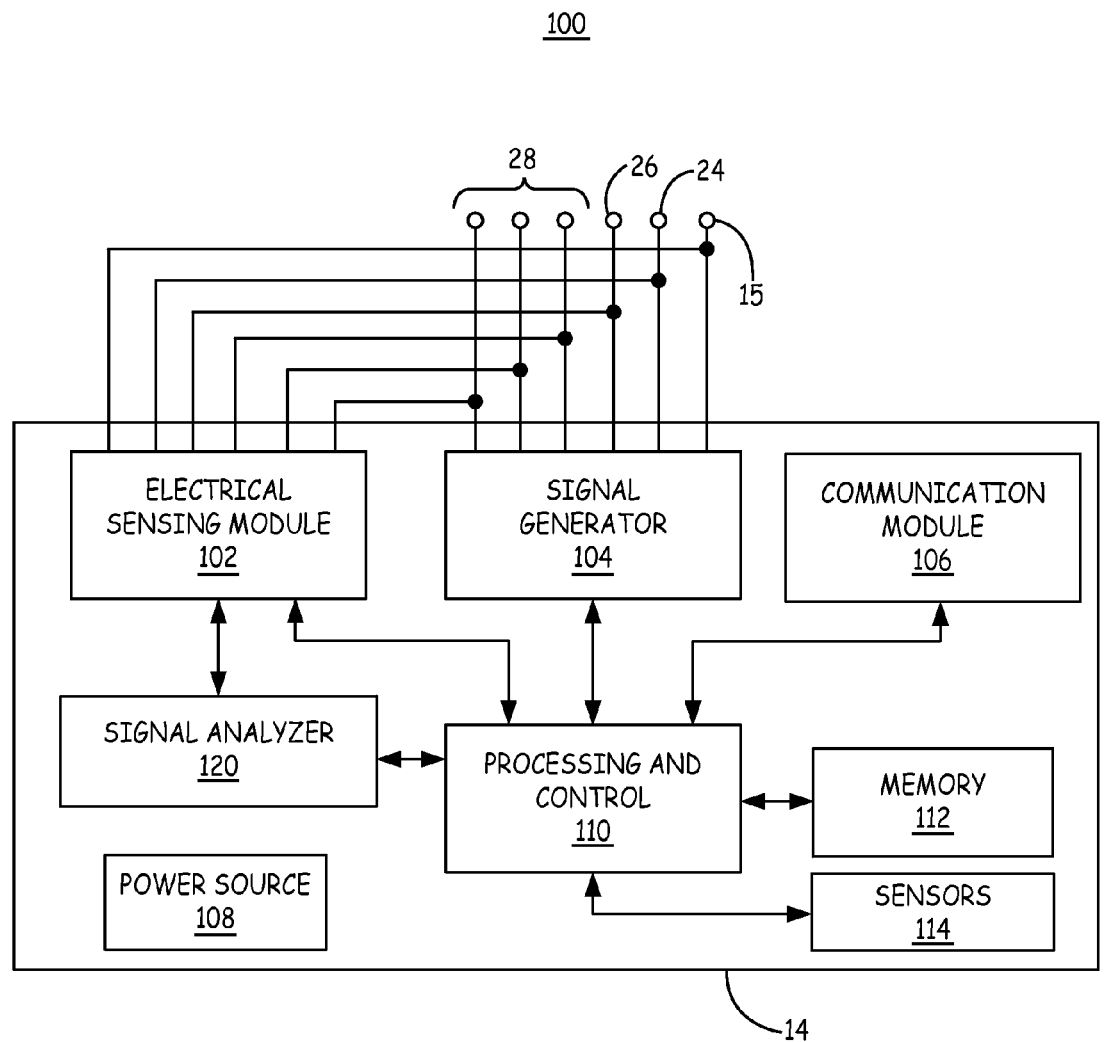
FIG. 3 is a functional block diagram of electronic circuitry that is included in one embodiment of IMD 14 shown in FIG. 1 for practicing the methods described herein.

FIG. 3 is a functional block diagram 100 of electronic circuitry that is included in one embodiment of IMD 14 shown in FIG. 1 for practicing the methods described herein. The IMD 14 includes electrical sensing module 102, signal generator module 104, communication module 106, processing and control module 110 and associated memory 112, and cardiac signal analyzer 120. A power source 108 provides power to each of the modules 102, 104, 106, 110, 112, 114 and 120. Power source 108 may include one or more energy storage devices, such as one or more primary or rechargeable batteries.

Modules 102, 104, 106, 110, 112, 114 and 120 represent functionality included in IMD 14. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, integrated circuits, a processor (shared, dedicated, or group) that executes one or more software or firmware programs, memory devices, or any other suitable components or combination thereof that provide the described functionality.

Memory 112 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Furthermore, memory 112 may include non-transitory computer readable media storing instructions that, when executed by one or more processing circuits, cause the modules to perform various functions attributed to IMD 14.

Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, tachyarrhythmia detection processes performed by cardiac signal analyzer 120 may be implemented in a processing and control module 110 executing instructions stored in memory 112.

Processing and control module 110 communicates with signal generator module 104, cardiac signal analyzer 120 and electrical sensing module 102 for sensing cardiac electrical activity, detecting cardiac rhythms, and generating cardiac therapies in response to sensed signals. Signal generator module 104 and electrical sensing module 102 are electrically coupled to subcutaneous electrodes 28 incorporated along but electrically insulated from IMD housing 15, lead-based electrodes 24 and 26 and housing 15, at least a portion of which also serves as a common or ground electrode and is therefore also referred to herein as "housing electrode" 15.

Electrical sensing module 102 is configured to monitor signals from available electrodes 26 and 28 (or other available sensing electrodes) in order to monitor electrical activity of a patient's heart. Electrical sensing module 102 may selectively monitor one or more sensing vectors selected from available electrodes. Sensing module 102 may include switching circuitry for selecting which of electrodes 24, 26, 28 and housing electrode 15 are coupled to sense amplifiers included in sensing module 102. Switching circuitry may include a switch array, switch matrix, multiplexer, or any other type of switching device suitable to selectively couple sense amplifiers to selected electrodes. Sensing vectors will typically be selected from SEA electrodes 28 in combination with lead-based sensing electrode 26 although it is recognized that in some embodiments sensing vectors may be selected that utilize coil electrode 24 and/or housing electrode 15.

Sensing module 102 provides sense event signals corresponding to the timing of sensing R-waves (and P-waves in some embodiments) and digitized ECG signals to cardiac signal analyzer 120 for detecting and discriminating cardiac rhythms. Some aspects of sensing and processing subcutaneous ECG signals are generally disclosed in commonly-assigned U.S. Pat. No. 7,904,153 (Greenhut, et al.), hereby incorporated herein by reference in its entirety. Processes performed by signal analyzer 120 for detecting and discriminating tachyarrhythmia may include techniques generally disclosed in U.S. Pat. No. 7,742,812 (Ghanem, et. al) and U.S. Pat. No. 8,160,684 (Ghanem, et. al), both of which patents are incorporated herein by reference in their entirety.

Electrical sensing module 102 may include signal conditioning circuits, e.g., amplification and filtering circuits that amplify and filter cardiac electrical signals received from electrodes 26 and 28. Electrical sensing module 102 includes analog-to-digital (ND) conversion circuits that digitize the conditioned cardiac electrical signals. The digitized data generated by the ND circuits included in electrical sensing module 102 may be referred to as "raw data." In some examples, the A/D circuits may include an 8-bit A/D converter that samples conditioned cardiac electrical signals at approximately 256 Hz. Sensing module 102 generates R-wave sense signals upon sensing an R-wave from the ECG signal, for example based on an auto-adjusted threshold crossing of the ECG signal. The timing of an R-wave sense signal may be used by signal analyzer 120 to measure R-R intervals for counting RR intervals in different detection zones or estimating a heart rate or other rate-based measurements for detecting tachyarrhythmia. The timing of R-wave sense signals may additionally or alternatively be used by signal analyzer 120 for setting morphology analysis windows in some embodiments. Signal analyzer 120 may receive and analyze digitized ECG signals over n-second windows independent of R-wave sense event timing.

In some embodiments, sensing module 102 may include multiple sensing channels having different sensing bandwidths. The different sensing channels may be coupled to the same or different sensing electrode vectors selected from SEA electrodes 28 and lead-based sensing electrode 26. In one embodiment, sensing module 102 includes a wide-band channel having a bandwidth of approximately 2.5 Hz to 95 Hz and a narrow-band channel having a sensing bandwidth between 2.5 Hz and 23 Hz. Both channels may be used for providing digitized raw ECG signals to cardiac signal analyzer 120 for performing morphology analysis. Alternatively, the wide band channel or the narrow band channel may be used alone for performing the morphology analysis. In some embodiments, a third channel having a third pass band different than the morphology signal channels is used for sensing R-wave signals. For example, an R-wave sensing channel may have a pass band intermediate the narrow band and wide band sensing channels, e.g., approximately 10 Hz to 32 Hz.

Cardiac signal analyzer 120 receives R-wave sense signals and raw ECG signals from electrical sensing module 102 and detects cardiac tachyarrhythmia based on the R-wave sense signals and raw ECG signals and processing thereof. As further described below, cardiac signal analyzer 120 initially operates in a safety and learning process that utilizes a tachyarrhythmia detection algorithm relying on population-based detection thresholds to promote patient safety (i.e., provide a high sensitivity of detecting and treating life-threatening arrhythmias) while simultaneously acquiring cardiac signals for establishing patient-based detection thresholds.

Once a required set of patient-based detection thresholds is established, the operating mode of signal analyzer 120 converts to an evolving patient-specific detection process that includes patient-specific thresholds and may additionally include population-based threshold(s). The evolving detection process executes a different detection algorithm than the initial safety detection process. At least one detection criterion that requires a patient-specific threshold is not used or applied in the initial safety detection process and is applied during the patient-specific detection process. The patient-specific detection process is referred to as an "evolving" process in that patient-specific thresholds may be updated and/or new patient-specific thresholds may be added for use by the evolving detection process as they become available. The patient-specific detection process is expected to provide higher specificity in detecting and discriminating between shockable and non-shockable rhythms than the initial safety detection process.

As used herein, the term "shockable rhythm" refers to malignant or life threatening ventricular tachyarrhythmia, which can be terminated by shock delivery with a high probability. "Non-shockable" rhythm refers to non-malignant heart rhythms that are not life threatening, such as SVT. In some embodiments, other therapies besides a shock therapy may be used, at least initially, to treat a shockable VT, such as anti-tachycardia pacing therapy (ATP). Accordingly, a "shockable" rhythm could alternatively be referred to as a "treatable" rhythm in that a cardioversion/defibrillation shock may not be the only therapy being utilized to treat a "shockable rhythm." A "non-shockable" rhythm may alternatively be referred to as an "untreated" rhythm since it is not perceived to be a rhythm that is threatening to the patient and is therefore not treated by IMD 14.

When signal analyzer 120 detects a tachyarrhythmia, a detection signal is provided to processing and control module 110 indicating the current detection state as SVT (non-shockable) or VT or VF (shockable). Processing and control module 110 will respond to a VT or VF detection signal from signal analyzer 120 according to a programmed menu of therapies. Control module 110 will control signal generator 104 to deliver a therapy accordingly, e.g. a cardioversion or defibrillation shock pulse using coil electrode 24 and housing electrode 15.

It should be noted that implemented tachyarrhythmia detection algorithms may utilize signals from supplemental sensors 114 in addition to ECG signals. Supplemental sensor signals may include tissue or blood oxygenation signals, respiration, patient activity, heart sounds, heart wall motion, and the like. These secondary sensors may contribute to a decision by processing and control module 110 to apply or withhold a therapy. In particular, in one embodiment, during the initial safety and learning process, the processing and control 110 may verify a rhythm state based on the secondary sensor signals. In some embodiments, patient-specific detection thresholds may include thresholds determined from non-ECG signals sensed from sensors 114.

Signal analyzer 120 may receive a signal from an activity sensor included in sensors 114 and generate a shockable rhythm detection signal only in response to a low activity signal in combination with other ECG-based detection criteria being satisfied during the population-based, initial safety detection process. In other examples, a non-ECG signal indicative of a worsening hemodynamic condition or mechanical cardiac function may be used to corroborate ECG-based detection threshold evidence for detecting shockable VT or VF.

In response to VT or VF detection as described above, processing and control module 110 may control signal generator module 104 to deliver a shock therapy using coil electrode 24 and housing electrode 15 according to one or more therapy programs, which may be stored in memory 112. For example, processing and control module 110 may control signal generator module 104 to deliver a shock pulse at a first energy level and increase the energy level upon redetection of a VT or VF rhythm. Shock pulse generation and control is further described in the above incorporated '153 Greenhut patent. In some embodiments, IMD 14 or other implantable medical device operating according to the detection techniques described herein may be capable of delivering other tachyarrhythmia therapies, ATP, in response to a VT detection signal from signal analyzer 120.

Communication module 106 includes any suitable hardware, firmware, software or any combination thereof for communicating with another device, such as an external programmer 20 and/or a patient monitor. Under the control of processing module 110, communication module 106 may receive downlink telemetry from and send uplink telemetry to programmer 20 and/or a patient monitor with the aid of an antenna (not shown) in IMD 14.

Processing and control module 110 may generate marker channel data based on analysis of the raw data. The marker channel data may include data that indicates the occurrence and timing of sensing, diagnosis, and therapy events associated with IMD 14. Processing and control module 110 may store the generated marker channel data in memory 112. Although not illustrated, in some examples, marker channel data may include information regarding the performance or integrity of IMD 14, including power source 108 and lead 18.

Processing and control module 110 may store raw data and marker channel data in memory 112. For example, processing and control module 110 may continuously store raw data from one or more electrode combinations in memory 112 as the raw data is received from electrical sensing module 102. In this manner, processing and control module 110 and cardiac signal analyzer 120 may use memory 112 as a buffer to store a predetermined amount of raw data. In some examples, processing and control module 110 may store raw data corresponding to a predetermined number of cardiac cycles, e.g., 12 cycles, or a desired number of predetermined time intervals of raw data. In other examples, processing and control module 110 may store a predetermined number of samples of raw data. Raw data buffered in memory 112 may be accessed by signal analyzer 120 for establishing patient-specific detection thresholds during the initial population-based safety detection and learning process, for performing morphology analysis for detecting VT and VF during the patient-specific detection process, and for updating patient-specific thresholds during the evolving patient-specific detection process as will be further described herein.

Figure 4:
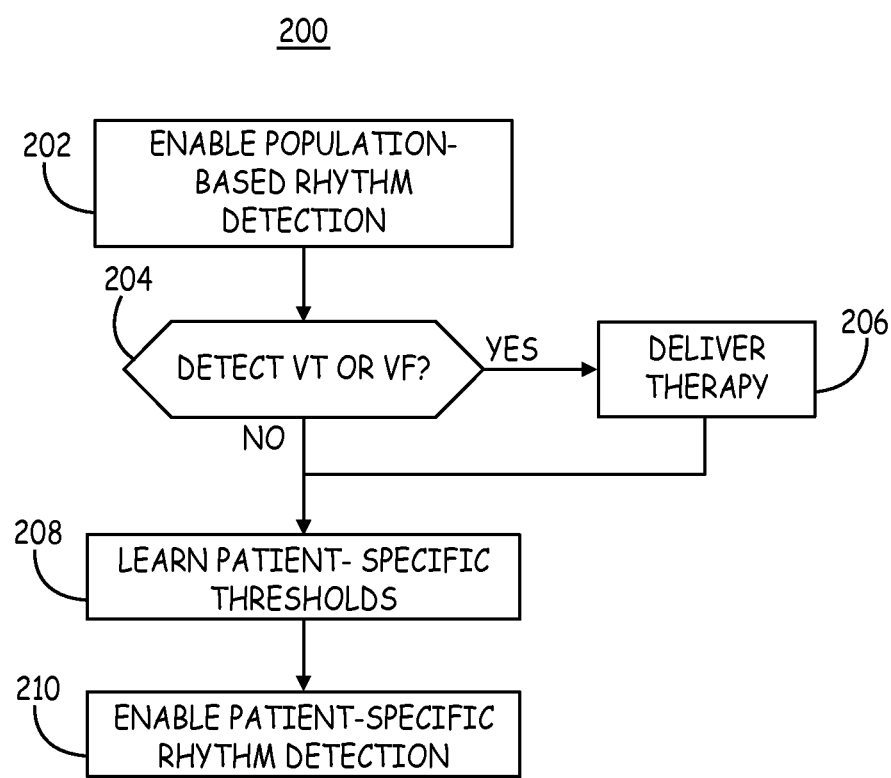
FIG. 4 is a flow chart of a method for detecting tachyarrhythmia according to one embodiment.

FIG. 4 is a flow chart 200 of a technique for controlling detection of tachyarrhythmia according to one embodiment. Flow chart 200 and other flow charts presented herein are intended to illustrate the functional operation of the device, and should not be construed as reflective of a specific form of software or hardware necessary to practice the methods described. It is believed that the particular form of software, firmware, hardware or combination thereof will be determined primarily by the particular system architecture employed in the device and by the particular signal sensing and therapy delivery methodologies employed by the device. Providing software, firmware, and/or hardware to accomplish the described functionality in the context of any modern medical device, given the disclosure herein, is within the abilities of one of skill in the art.

Methods described in conjunction with flow charts presented herein may be implemented in a non-transitory computer-readable storage medium that stores instructions for causing a programmable processor to carry out the methods described. A computer-readable storage medium includes but is not limited to any volatile or non-volatile media, such as a RAM, ROM, CD-ROM, NVRAM, EEPROM, flash memory, and the like with the sole exception being a transitory, propagating signal. The instructions may be implemented as one or more software modules, which may be executed by themselves or in combination with other software.

Upon implantation of IMD 14, the cardiac signal analyzer 120 automatically operates in a first detection process, referred to as the initial safety detection and learning process, which includes a population-based rhythm detection algorithm. In some embodiments, the population-based rhythm detection algorithm does not include any patient-specific detection thresholds or programmed detection thresholds or parameters. Detection criteria are not tailored to a specific patient, but are based on data from a population of patients resulting in a high sensitivity to detecting shockable rhythms.

The population-based detection criteria may be established to provide high sensitivity to detecting shockable rhythms while sacrificing specificity in order to provide the greatest protection to the patient for treating potentially lethal rhythms during this initial mode of operation. In some embodiments, the initial safety detection process requires no programming on the part of a clinician. The detection thresholds are population-based thresholds stored in the device at the time of manufacture and need not be changed to provide tachyarrhythmia detection in a safety mode. If a shockable VT or VF rhythm is detected, as determined at block 204, according to the population-based detection criteria, therapy is delivered at block 206.

During the population-based, safety rhythm detection and learning process, one or more patient-specific thresholds are learned at block 208. A patient-specific threshold is learned by determining an ECG signal feature representative of the patient's heart rhythm during known conditions and setting a detection threshold based on the representative ECG signal feature. The patient-specific thresholds may be learned during a non-shockable rhythm, e.g. normal sinus rhythm (NSR) or SVT, i.e. when VT or VF is not being detected and therapy is not being delivered. A non-shockable rhythm ECG signal feature may be determined, and a corresponding patient-specific detection threshold may be set to a value based on, but different than, the non-shockable ECG feature value. The threshold may set to a value expected to represent a change in the signal feature that would occur during a shockable rhythm. The patient-specific threshold can be based on a range and/or variability of the determined signal feature during a non-shockable rhythm.

In other embodiments, the ECG signal acquired during a VT or VF rhythm may also be used for establishing patient-specific thresholds at block 208. For example, when a shockable rhythm is detected by the population-based, initial safety detection process, a patient-specific detection threshold may be verified as an appropriate threshold based on the ECG signal feature determined during the shockable rhythm. The shockable rhythm may be confirmed using other, non-ECG signals (e.g. a hemodynamically unstable rhythm based on a hemodynamic sensor) to avoid adjustment of a patient-specific threshold based on a falsely detected shockable rhythm. The range and/or variability of the ECG signal feature during the shockable rhythm may be used to adjust or confirm an appropriate patient-specific detection threshold.

Additional details regarding the process of learning patient-specific thresholds will be described below. After establishing patient-specific thresholds, a detection algorithm that relies on detection criteria including at least one patient-specific threshold is enabled at block 210. The cardiac signal analyzer 120 stops operating the population-based safety detection process and starts operating the patient-specific detection process. The patient-specific detection process is a different algorithm than the population-based detection algorithm; the patient-specific process utilizes a different set of detection criteria that requires more than a mere substitution of a population-based threshold value for a patient-specific threshold value. In other words, the set of cardiac signal features determined and compared to designated thresholds during the patient-specific detection process is a different set of cardiac signal features than that determined during the initial population-based safety detection algorithm.

In an illustrative embodiment, during an initial safety detection process, the IMD cardiac signal analyzer 120 may detect a shockable cardiac rhythm by comparing the cardiac signal to a first set of detection criteria including, for each criterion of the first set of detection criteria, only population-based detection thresholds. During this initial, population-based rhythm detection process, the processing and control unit 110 establishes at least one patient-specific detection threshold. Upon establishing at least one patient-specific detection threshold required for operating a patient-specific rhythm detection algorithm, the processing and control unit stops the initial detection process and starts a rhythm detection process that includes a criterion relating to the patient-specific detection threshold that was not included in the initial safety detection process. The acquired cardiac signal, an ECG signal in this example, is compared to a different set of detection criteria, including at least one criterion that requires a learned patient-specific detection threshold and is not a criterion used by the population-based, initial safety detection process.

Figure 5:
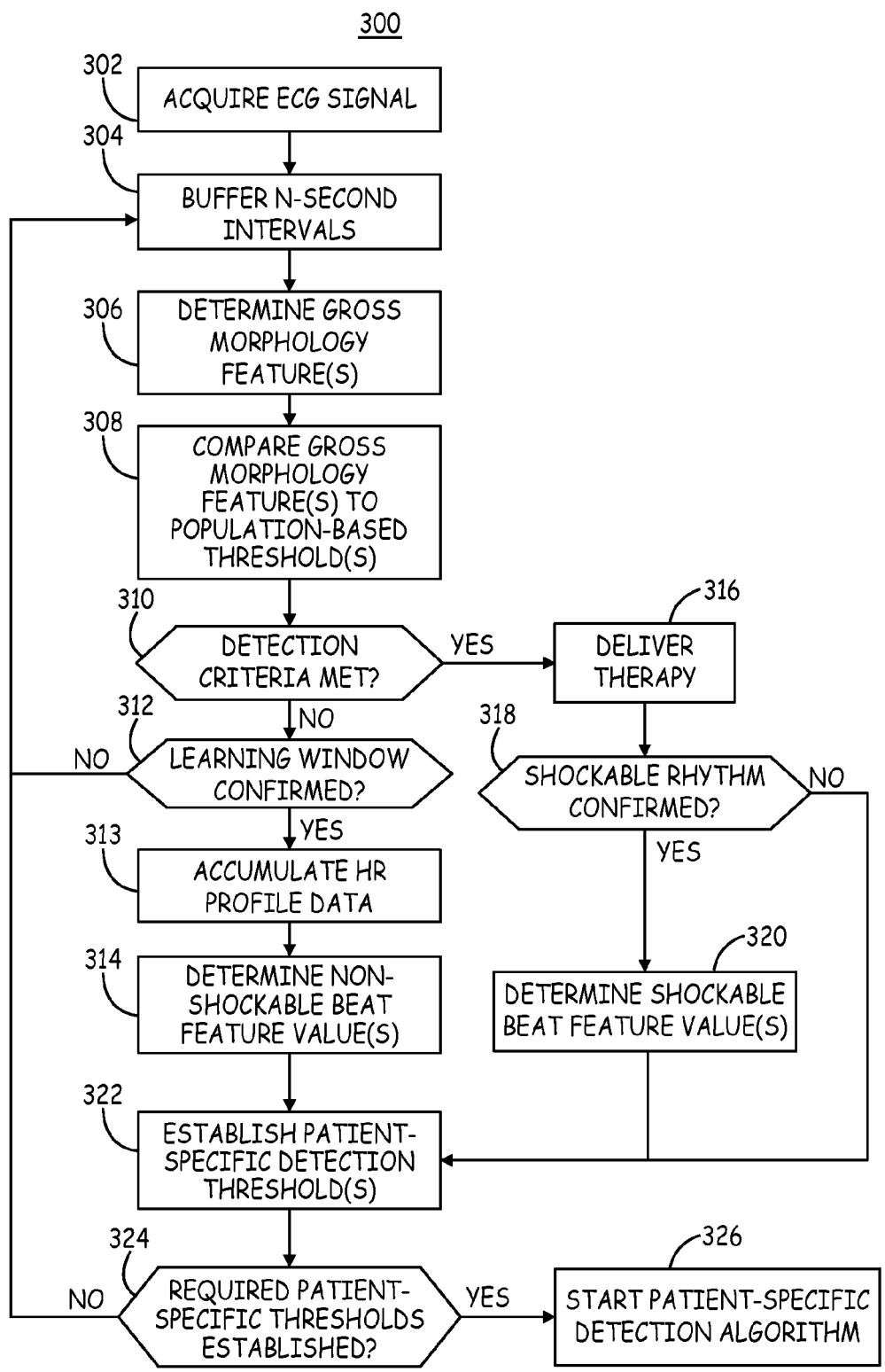
FIG. 5 is a flow chart of a method for detecting tachyarrhythmia according to an alternative embodiment.

FIG. 5 is a flow chart 300 of a method for detecting tachyarrhythmia according to an alternative embodiment. An ECG signal is acquired at block 302. As described above, in some embodiments, two or more ECG signals are sensed using different sensing vectors. Multiple sensing channels having different bandpass properties may be used for acquiring ECG signals from one or more sensing vectors. When referring to analysis of an ECG signal, it is understood that this analysis may apply to one or more ECG signals acquired from different vectors and/or sensing channels. All or portions of the analysis may be performed on one or more signals in any combination. In other words, some ECG signal features may be determined from one sensing vector or signal channel while the same or different ECG signal features may be determined from a different sensing vector and/or sensing channel.

During the initial safety detection process, the ECG signal is segmented into n-second intervals, e.g. 3 second intervals, and the n-second intervals are buffered in IMD memory at block 304. The n-second intervals are used for determining gross morphology features during the initial safety detection process. Gross morphology features are determined across an n-second time interval without relying on R-wave sensing and are therefore features that can be determined from the ECG signal independent of the cardiac cycle. The n-second window may start and end at any time point relative to an R-wave sense signal. Morphology features computed across the n-second time period are referred to as "gross" morphology features because the features are characteristics of the signal that are extracted, independent of cardiac cycle timing, from a time segment that includes multiple cardiac cycles. In contrast, morphology features extracted from the ECG signal during a cardiac cycle are referred to as "beat" morphology features. Beat morphology features are determined from an ECG signal segment over a time interval of one cardiac cycle. Beat morphology features may be averaged or determined from multiple cardiac cycles but are representative of a feature of the ECG signal during a cardiac cycle. Determination of a beat feature is dependent on identifying the timing of a cardiac cycle, or at least a sensed event such as an R-wave, as opposed to determining gross features independent of the cardiac cycle over a time segment that is typically longer than one cardiac cycle.

Examples of gross morphology analysis that may be implemented in an initial safety detection process are generally disclosed in U.S. Pat. No. 7,742,812 (Ghanem, et. al) and U.S. Pat. No. 8,160,684 (Ghanem, et. al), both of which patents are incorporated herein by reference in their entirety. In one embodiment, the cardiac signal analyzer 120 analyzes the frequency content of the raw ECG signal across the n-second time period. For example, a low slope content may be determined. The low slope content may be approximated as the ratio of the number of slope data points less than a low slope threshold to the total number of data points determined during the n-second time period. Slope data points are determined as the sample-to-sample differences of the raw ECG signal. In one example, the low slope threshold may be defined as a percentage, for example 10%, of the largest absolute slope determined from the signal segment. The low slope content is then determined as the number of slope data points having an absolute value less than the low slope threshold to the total number of slope data points occurring in the n-second analysis time period.

The low slope content of non-shockable tachyarrhythmia is typically high relative to the low slope content of shockable tachyarrhythmia. As such, the low slope content is a useful ECG signal parameter to monitor for determining when a shock therapy is needed. In one embodiment, the low slope content is determined for at least two consecutive n-second time periods.

If the low slope content of two consecutive n-second time periods, or at least two of the most recent three n-second time periods is less than a population-based detection threshold, the cardiac signal analyzer 120 may provide a shockable rhythm detection signal to control module 110. The population-based detection threshold is pre-defined as a low slope content below which a majority of patients would be experiencing a shockable rhythm.

In other embodiments, frequency content of the n-second time periods may be evaluated by determining a ratio of high versus low frequency power, mean frequency or spectral width estimation, or probability density function to determine if the frequency content meets a population-based shockable rhythm detection criterion. One or more gross morphology features may be determined and compared to respective shockable rhythm detection criteria based on a population of patients. If gross morphology detection criteria are satisfied for a threshold number of consecutive n-second segments or some ratio of n-second segments, as determined at block 310, a shockable rhythm is detected. Therapy is delivered at block 318.

The detection criteria applied at block 310 include only population-based thresholds without any patient-specific thresholds being used by the initial safety detection process. While not shown explicitly in FIG. 5, it is contemplated that a rate based requirement for detecting a shockable rhythm may be defined in addition to gross morphology detection requirements. For example, the heart rate may be required to exceed a shockable rhythm heart rate threshold before detecting a shockable rhythm. Rate or RR-interval detection requirements are also defined according to population based thresholds. In other words, a majority of patients would be experiencing a shockable rhythm when an estimated heart rate exceeds the population-based rate threshold or when a required number of RR intervals are shorter than a population-based detection interval The initial safety detection process is a detection process intended to detect all potentially lethal tachyarrhythmia with a high probability thereby providing a "safety net" to the patient while patient-specific detection thresholds are being learned automatically by the IMD, without requiring any programming of detection parameters by a clinician. The safety detection process may compromise specificity in discriminating SVT, VT and VF in order to achieve high sensitivity to shockable rhythm detection using population-based detection thresholds.

If a shockable rhythm is not being detected during the initial safety detection process, a "learning window" is set at block 312. The processor and control 110 may use other sensor signals at block 312 to confirm a non-shockable rhythm. Non-shockable rhythms may include normal sinus rhythm, sinus tachycardia, or SVT such as atrial fibrillation. Non-shockable rhythm types may or may not be discriminated from each other by the confirmation process. During a confirmed non-shockable rhythm, patient-specific ECG signal features may be determined. Multiple learning windows may be set by processor and control module 110 to enable the signal analyzer 120 to determine patient-specific features during different non-shockable rhythm conditions, e.g. NSR at rest (low resting heart rate), NSR during moderate exercise such as walking (moderate heart rate), NSR during relatively higher activity (high heart rate), and SVT.

As such, heart rate may be determined from R-R intervals sensed from an ECG signal or estimated from the n-second intervals. A patient's heart rate profile, i.e. heart rate range and variability, can be established from determined heart rates. An activity signal may be used to confirm an activity state corresponding to a determined or estimated heart rate. An ECG-derived respiration rate may be used in addition to or alternatively to an activity sensor signal for confirming heart rate conditions desired for learning patient-specific features. In this way, ECG signal features corresponding to different sinus rates may be learned for the given patient.

Additionally or alternatively, other non-ECG signals such as a heart sound sensor, an accelerometer measuring heart wall motion, a blood pressure sensor, an oxygen sensor, or other hemodynamic or mechanical sensors, may be used to confirm a non-shockable rhythm. Confirming a learning window may further include noise analysis to reduce the likelihood of determining patient-specific ECG signal features during noise-corrupted cardiac cycles. For example, a threshold number of noise spikes may prevent a learning window from being set. All available signals sensed by sensors coupled to the IMD may be analyzed to confirm (or at least not invalidate) desired conditions for setting a learning window. A non-shockable rhythm may be confirmed retrospectively by an expert viewing recorded signals retrieved from the IMD, and this confirmation may be subsequently used to confirm learned patient-specific thresholds.

If a heart rate, activity level, respiration rate, signal quality, and/or other learning window conditions cannot be confirmed based on the ECG signal and other available sensor signals, the process returns to block 304 to continue monitoring n-second intervals for population-based rhythm detection. A learning window is not set and patient-specific ECG signal features are not determined at the present time.

When a learning window is confirmed at block 312 as being sinus rhythm (or a non-shockable rhythm), data for establishing a patient-specific heart rate (HR) profile may be acquired at block 313. HR profile data may be used for establishing boundaries between sinus tachycardia or non-shockable rhythms and ventricular tachyarrhythmia or shockable rhythms. The HR profile data is acquired to establish a patient's individual cut-off heart rate for detecting tachyarrhythmia. This cut-off heart rate may be established over a relatively longer period of time than the time required to establish other patient-specific detection thresholds as described below in that gradual changes in a patient's sinus heart rate range may occur with changing heart condition, changes in prescription drugs and other factors. As HR profile data is accumulated, however, a HR cutoff for tachyarrhythmia detection may be increased from a nominal population-based value, based on confirmation of sinus rhythm during activity, or decreased from a nominal value, based on sinus rates never going as high as the nominal value.

If a learning window is confirmed at block 312, non-shockable ECG signal features are determined at block 314. In one example, the patient-specific thresholds established for a patient-specific detection process rely on beat features that correspond to a cardiac cycle in contrast to the gross morphology features determined over an n-second interval independent of the cardiac cycle. Beat features may include, but are not limited to, an R-wave morphology template, R-wave width, QRS width, Q-T interval, Q-T interval to RR interval ratio, R-wave amplitude to T-wave amplitude ratio, R-wave polarity, and Q-wave amplitude to R-wave amplitude ratio.

Patient-specific beat features may be measured for one or more cardiac cycles during the confirmed learning window. Features may be averaged over multiple cycles or non-parametric measurements may be used, e.g. determining the nth largest feature out of m cardiac cycles. As described further below, more than one learning window may be required for determining patient-specific features.

Once patient specific features are determined for a desired number of learning windows, patient-specific detection thresholds are established at block 322 based on the determined features. The patient-specific detection thresholds may define boundaries or ranges for a given feature that are used to discriminate between shockable and non-shockable rhythms. A patient-specific detection threshold may be set as a change from a baseline non-shockable beat feature determined at block 314. For example, a patient-specific detection threshold may be defined as a percentage change from a non-shockable rhythm beat feature.

In some embodiments, patient-specific features may also be determined during a confirmed shockable rhythm. For example, when a shockable rhythm is detected in response to the population-based detection algorithm, shockable beat features may be determined at block 320 using the ECG signal segments that resulted in a shockable rhythm detection and/or corresponding R-wave sense events. In some embodiments, shockable rhythm detection may be confirmed at block 316, prior to shock delivery (block 318), using secondary sensors, such as mechanical, hemodynamic or activity sensors before determining shockable beat features. If patient-specific features are available from both confirmed shockable rhythm learning window(s) and from non-shockable rhythm learning window(s), a comparison between the analogous features may be made when establishing patient-specific detection thresholds. For example, a boundary between a shockable range of a given patient-specific feature and a non-shockable range of the patient-specific feature may be defined between the shockable feature value and its range and the non-shockable feature value and its range.

If the required detection thresholds needed to operate a patient-specific detection process have been established, as determined at decision block 324, the patient-specific detection process is started at block 326. The initial safety detection process based on population-based thresholds applied to gross morphology features determined from n-second windows is terminated. The patient-specific detection process relies on analysis of cardiac cycle beat features and corresponding patient-specific thresholds. The patient-specific detection process may additionally rely on gross morphology analysis of n-second segments using any combination of population-based and patient-specific thresholds. The patient-specific process is a different process than the initial safety detection process since a different set of features must be determined from the ECG signal. In the illustrative embodiment, the different set of features determined from the ECG signal includes at least one beat feature not used by the initial safety detection process.

Figure 6:
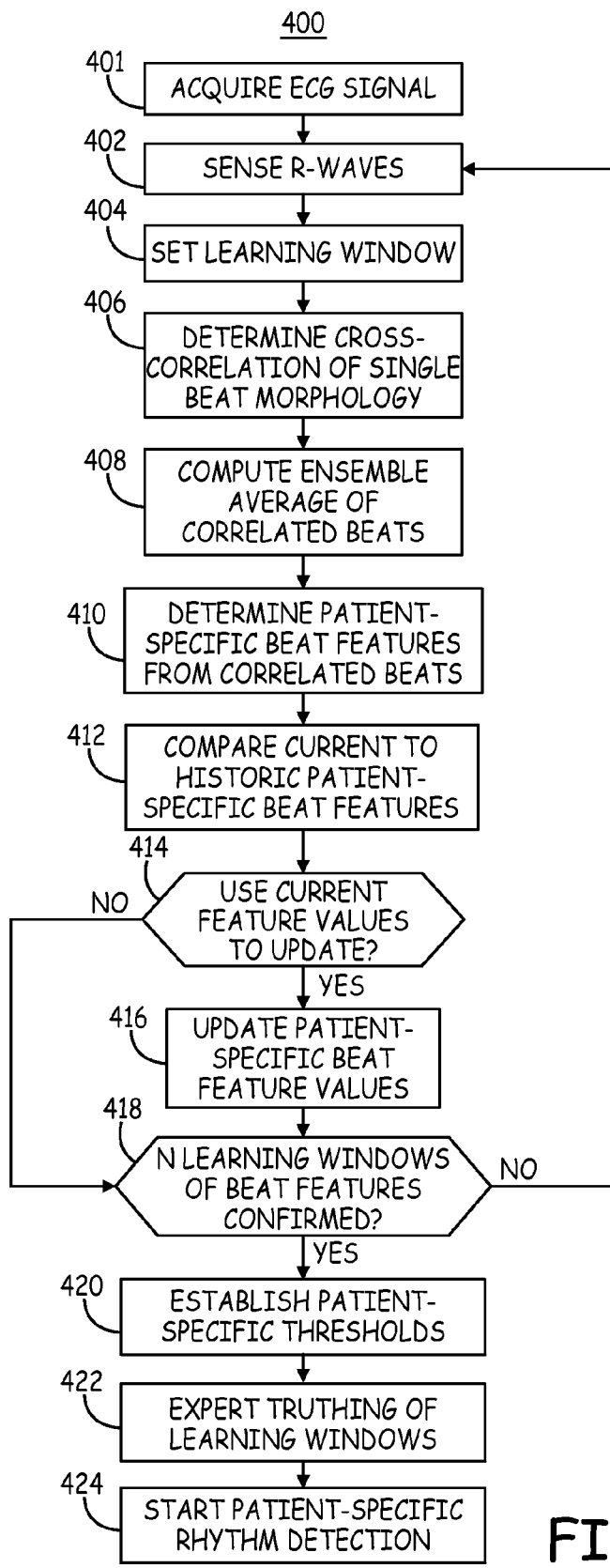
FIG. 6 is a flow chart of a method for establishing patient-specific detection thresholds according to one embodiment.

FIG. 6 is a flow chart 400 of a method for establishing patient-specific detection thresholds according to one embodiment. The patient-specific detection thresholds are established during the initial, population-based safety detection process. As such, the method shown by flow chart 400 is operating during the initial detection process. Additionally, portions of the method shown by flow chart 400 may be performed during the patient-specific rhythm detection process for updating patient-specific detection thresholds over time.

At block 401, one or more ECG signals are acquired and R-wave signals are sensed from the ECG signal(s) at block 402. A learning window is set at block 404 after confirming learning conditions, as described above, based on one or more of an ECG-derived heart rate, ECG-derived respiration rate, activity, hemodynamic sensor, or any combination of available sensor signals.

Patient-specific beat features used by the patient-specific detection process may include a beat morphology template and associated beat matching score threshold(s) or range(s). Sensed R-waves may be used for setting a morphology window, e.g. approximately centered on an R-wave sense signal for each R-wave of all or a predetermined number of sensed R-waves occurring during the learning window. A cross-correlation of each single beat morphology to each of the other beats within the learning window may be performed at block 406 to determine a similarity between the beats. Beats meeting a minimum correlation with a minimum number of the total beats within the learning window may be selected as representing the dominant "normal" morphology within the learning window.

For example, a first beat signal may be selected and compared to each of the other beats in the learning window. If the first beat meets a minimum correlation with at least half of the other beats (or another predetermined proportion of the total beats in the learning window), the correlated beats, i.e. similar beats, may be used for determining a beat template. If this requirement is not met, a different beat is selected and compared to other beats within the learning window. When selecting a different beat for comparison, a beat may be chosen that had a low correlation with the first beat that failed to meet the correlation criteria in an attempt to identify a different beat morphology that may be a better representation of the normal morphology during the learning window. This process may continue until a correlation requirement is met or a threshold number of beats have been compared to all other beats in search of similar beats for use in generating a template representative of a cardiac cycle signal during the learning window.

A beat morphology template is computed at block 408. The morphology template may be computed as an ensemble average of the ECG signal during the morphology window of all or a predetermined number of beats meeting the correlation or similarity requirements for the current learning window. In this way, a patient-specific beat morphology template is generated, representing the dominant normal R-wave morphology for the learning window. The beat morphology template may be learned first, prior to learning other beat features, to enable beats correlated to the dominant "normal" morphology, e.g. the morphology occurring with the highest rate of incidence, during the current learning window to be used for determining other beat features.

Other patient-specific beat features are determined at block 410. A predetermined number of sinus beats may be required for determining a patient-specific feature. For example, at least sixteen, thirty-two, or other specified number of cycles identified as meeting a cross-correlation requirement may be averaged or used in combination for determining a patient-specific feature. If the required number of correlated beats cannot be identified during the current learning period, the current learning period may be discarded and not used for establishing patient-specific ECG feature values.

If the required number of correlated beats is obtained, patient-specific features are computed for the current learning window. In some embodiments, additional patient-specific beat features are extracted from the beat morphology template. In other embodiments, patient-specific beat features are computed from a required number of beats meeting the correlation requirement or from those beats used to compute the beat morphology template. In one example, patient-specific beat features determined at block 410 include QRS width, Q-T interval, Q-T interval as a proportion of R-R interval, ratio of R-wave amplitude to T-wave amplitude, R-wave polarity, ratio of Q-wave amplitude to R-wave amplitude, and the average heart rate for the learning period (or for only the correlated cardiac cycles used for determining beat features).

Each beat feature value determined for the current learning window is compared to one or more historic beat features at block 412. In order to prevent inappropriate learning of invalid or non-representative values of normal beats, the current beat feature values are compared with historic feature values to promote a high likelihood of valid patient-specific beat features before establishing patient-specific detection thresholds based on those beat features. If one or more currently determined beat feature values differs from an analogous historic value by more than a predetermined amount, the current beat feature values may be rejected and not used for establishing patient-specific thresholds.

In some embodiments, the learning process includes multiple learning windows. For example, learning windows may be set and confirmed every eight hours for two consecutive days. At each eight hour interval, at least three learning windows may be set to obtain patient-specific feature values for a total of eighteen learning windows. The patient specific values obtained for the current learning window are compared to the historic values determined for each of the other seventeen learning windows, previously stored with a time stamp. If the current values are within an acceptable range of the historic values and/or within previously established physiological limits, they are used to update or establish the patient specific beat feature values at block 416.

The acceptance range for new beat feature values may initially be relatively wide and may become narrower as more data is collected. For example, new beat feature values may be accepted when within 30% of a historic value for the second through nth learning windows. The acceptance range may be required to be within 20% of the historic value for later learning windows, and ultimately within 10% of the historic value. In this way, the acceptance range for new beat feature values is adjusted as the historic value is updated. In particular, the range for accepting new feature values for updating a historic value is narrowed as the historic value is updated over time in some embodiments. The acceptance range may additionally or alternatively be dependent on a heart rate at which a new beat feature value was determined as compared to an average heart rate corresponding to a historic beat feature value. A larger heart rate difference would allow a larger acceptance range relative to the historic beat feature value.

Once patient-specific beat feature values are established using a minimum number of confirmed learning windows, the patient-specific thresholds for rhythm detection and discrimination are established at block 420. As described previously, a threshold may define a boundary between shockable and non-shockable rhythms or multiple boundaries or confidence zones may be defined for discriminating between SVT, VT and VF. The thresholds are set for each beat feature used by the patient-specific detection process and are based on the patient-specific beat feature values established at block 416. The beat feature values and thresholds may be updated at regular intervals as new learning windows are confirmed.

In some embodiments, learning the patient-specific thresholds is a fully automated process requiring no programming or intervention by a user, clinician or technician. In other embodiments, expert input is provided at block 422. Sample recordings of learning windows used to establish the thresholds and the threshold values may be transmitted to an external device for display and review by an expert. The expert may confirm that the learning windows correspond to desired learning conditions, that the learned feature values are valid, and confirm acceptance of the patient-specific threshold values prior to starting the patient-specific detection process.

Having established the patient-specific thresholds required to execute the patient-specific detection process, patient-specific rhythm detection is started at block 424. The initial safety detection process using only population-based detection thresholds is terminated. If a patient receives a replacement device, the patient specific thresholds may be transferred to the new device to provide immediate ideal behavior of the patient-specific rhythm detection process without having to repeat a learning process. The safety detection process will not be used again by the IMD for detecting shockable rhythms in some embodiments. In other embodiments, the IMD may revert to a safety detection mode if input from a patient, clinician or other sensor signals indicate that patient-specific detection thresholds need to be re-established.

In addition to establishing detection thresholds, the beat features may be used for ECG sensing vector quality assessment and selection and for setting auto-adjusting sensing threshold decay when the patient-specific detection process is started at block 424. For example, ECG sensing vectors and/or sensing channels may be identified that provide the highest signal-to-noise ratio of the beat features being determined. Different vectors/channels may be selected for determining different beat features based on the signal that provides the best resolution of the beat feature and separation of shockable and non-shockable values of the beat feature. Among the factors considered in selecting a vector are: R wave amplitude, greatest R/T ratio, least incidence of biphasic R-wave signals, better beat-by-beat correlation (similarity) than other vectors, and less variability of the beat features over time compared to other vectors.

In some embodiments, the decay rate of a self-adjusting threshold may be set based on learned R-wave and T-wave features. To illustrate, sensing module 102 may use a linearly decaying R-wave sensing threshold. The threshold may start, for example, at 65% of the sensed R wave amplitude after a 150 ms sensing refractory period following the R-wave sensed event. A learned R-T time interval enables determination of the time interval from the start of the decaying threshold (i.e. end of the sensing refractory period) to the T wave peak amplitude. The difference between the decaying threshold and the T-wave amplitude at the time of the T-wave can then be determined. If this difference is too small or negative, T-wave oversensing may occur. If the difference is too large, the decaying threshold could be adjusted to increase the sensitivity to low amplitude R-waves or fibrillation waves. The decay rate can be adjusted to avoid a rate that decays too fast resulting in T-wave oversensing or a rate that decays too slowly potentially resulting in undersensing of VF signals. In the former case, the decay rate can be decreased (slower decay) to avoid T-wave oversensing. In the latter case, the decay rate can be increased (faster decay) to reduce the likelihood of undersensing of R-waves and fibrillation waves while still avoiding T-wave oversensing.

Figure 7:
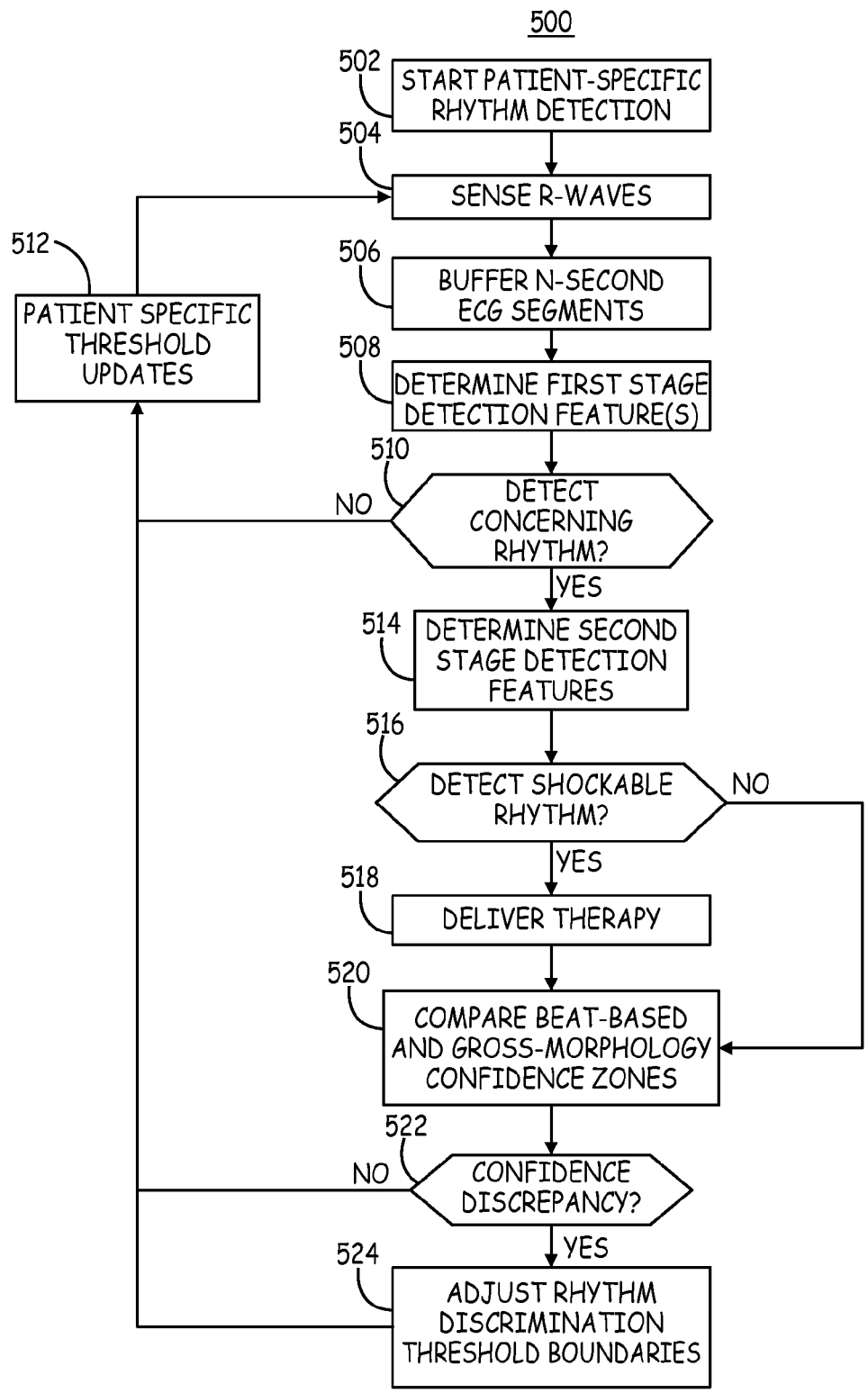
FIG. 7 is a flow chart of a patient-specific rhythm detection method according to one embodiment.

FIG. 7 is a flow chart 500 of a patient-specific rhythm detection process according to one embodiment. Upon starting patient-specific rhythm detection after establishing patient-specific thresholds, at block 502, R-waves are sensed from the ECG signal (block 504) and n-second ECG segments are buffered in memory (block 506) to provide cardiac signal analyzer 120 with R-wave sense signals for rate and beat feature analysis and ECG signal segments for gross morphology analysis.

In some embodiments, the patient-specific detection process includes a first stage for detecting concerning rhythms and a second stage for confirming or detecting the concerning rhythm as a shockable rhythm. The first stage includes a limited set of patient-specific detection criteria that requires relatively less complex signal analysis and/or processing burden compared to the second stage. For example, the first stage may include heart rate estimation, a limited set of beat features such as R-wave polarity, QRS- or R-wave width, and Q/R ratio or any other combination of beat features that are relatively simple to determine compared to more complicated analysis, such as morphology template matching or frequency analysis that may be included in the second stage. A subset of the patient-specific beat features for which patient-specific detection thresholds have been established may be determined during the first stage. The patient-specific detection process is expected to operate in the first stage a vast majority of the time, for example 99 percent of the time or more depending on the incidence of shockable rhythms in a given patient.

At block 508, the ECG signal features required for first stage analysis are determined. At block 510, the features are compared to the patient-specific detection thresholds established using the method shown in FIG. 6. A HR cutoff established from accumulated HR profile data may be compared to an estimated HR for detecting a concerning rhythm during the first stage. Additionally, one or more beat features may be compared to patient-specific thresholds for detecting a concerning rhythm.

In addition to comparing a limited set of feature values and estimated HR to patient-specific detection criteria, the first stage analysis may include detection of a sudden change in a beat feature, such as a sudden change in RR interval, R-wave width, R-wave polarity (positive, negative or biphasic) or other beat feature. A sudden change in an RR interval, R-wave width or other beat feature may indicate a concerning rhythm, i.e. a transition to a tachyarrhythmia. For example, a beat feature of the current cardiac cycle may be compared to the analogous beat feature of the nth previous cardiac cycle. A relative change in the beat feature over the n cardiac cycles, for example over 3 or 4 cardiac cycles, may be determined. If the relative change crosses a sudden onset detection threshold (e.g. a 50% or 100% change in the beat feature between the current beat and the third prior beat), then sudden change is detected.

As long as the first stage detection criteria are unmet, i.e. a concerning rhythm is not detected, the process remains in the first stage and may update patient-specific thresholds at block 512 as periodic learning windows are set as described above.

If detection criteria are met in the first stage, as determined at block 510, the process advances to the second stage for detecting and discriminating between shockable and non-shockable rhythms. Features of the sensed ECG signal are determined at block 514 as required by the second stage of the detection process. For example, all beat features for which patient-specific thresholds have been established may be determined and compared to the respective thresholds on a beat-by-beat basis and each beat may be compared to the patient-specific beat morphology template.

In some embodiments, gross morphology features may be determined from buffered n-second ECG segments by the signal analyzer during the second stage to provide detection of lethal VF rhythms using population-based gross morphology thresholds. It is further contemplated that patient-specific gross morphology thresholds may be established during the learning phase to replace population-based gross morphology thresholds during the patient-specific rhythm detection. Secondary sensors may also be analyzed during the second stage, such as activity, posture, heart sounds, blood pressure, oxygenation, or other available signals.

If shockable rhythm detection criteria are satisfied during the second stage of the patient-specific detection process, a therapy is delivered at block 518. If not, the process advances to block 520 without therapy delivery.

During or after the second stage, the confidence of rhythm detection outcomes from comparisons of beat features and patient-specific thresholds made during the second stage and the confidence of the rhythm detection outcomes from comparisons of gross morphology features and respective thresholds may be determined at block 520. For example, the confidence in detecting a shockable rhythm may be based on the number of features indicating a shockable rhythm and/or the amount that each signal feature exceeds a shockable rhythm detection threshold. Confidence zones may be defined as ranges of features values from near baseline indicating a high confidence that the rhythm is non-shockable, greater than a detection threshold indicating high confidence that the rhythm is shockable, and a gray zone near the shockable rhythm detection threshold but not crossing the threshold. Morphology matching score zones and other beat feature confidence zones may be defined based on the beat feature values and patient-specific thresholds.

The beat features may be individually or collectively rated as confident non-shockable, confident shockable, or gray zone. Likewise, gross morphology features may be rated as confident non-shockable, confident shockable, or gray zone. A comparison of the confidence zones of the patient-specific beat feature analysis and the gross morphology analysis, which may still be relying on population-based thresholds, may then be used to adjust rhythm discrimination threshold boundaries (block 524), when a confidence discrepancy exists, as determined at block 522.

For example, if the beat features indicate a confident shockable rhythm detection according to the patient-specific detection thresholds and the gross morphology features indicate a gray zone, the gross morphology detection thresholds, which may still be population-based thresholds, may be adjusted to include the values for the current rhythm as a confident shockable rhythm. In this way, population-based gross morphology thresholds may be gradually adjusted for the given patient to establish patient-specific thresholds for the gross morphology features.

In another example, if the beat feature analysis using patient-specific thresholds results in a gray zone non-shockable rhythm during the second stage and the gross morphology analysis results in a confident shockable rhythm, one or more patient-specific thresholds applied to the beat features may be adjusted. The patient-specific thresholds may be gradually adjusted to ensure safety in detecting lethal VF rhythms, particularly when a non-ECG signal can be used to confirm a shockable rhythm as detected by the gross morphology analysis.

In some embodiments, when a confidence discrepancy exists between the beat feature analysis and the gross morphology analysis, secondary signal analysis may be performed to determine which result is supported. Secondary signal analysis, such as patient activity level, patient posture, hemodynamic signal, blood or tissue oxygenation, heart sounds, or other signal(s) may support a confident shockable rhythm detection or a confident non-shockable detection, justifying an adjustment of threshold boundaries of either the beat feature thresholds or the gross morphology thresholds to correct any discrepancy between beat-based detection results and gross morphology detection results.

After any adjustments to the rhythm discrimination threshold boundaries at block 524, the process returns to operate in the first stage. Patient-specific thresholds may be updated periodically at block 512 during periodic confirmed learning windows as described previously.

Figure 8:
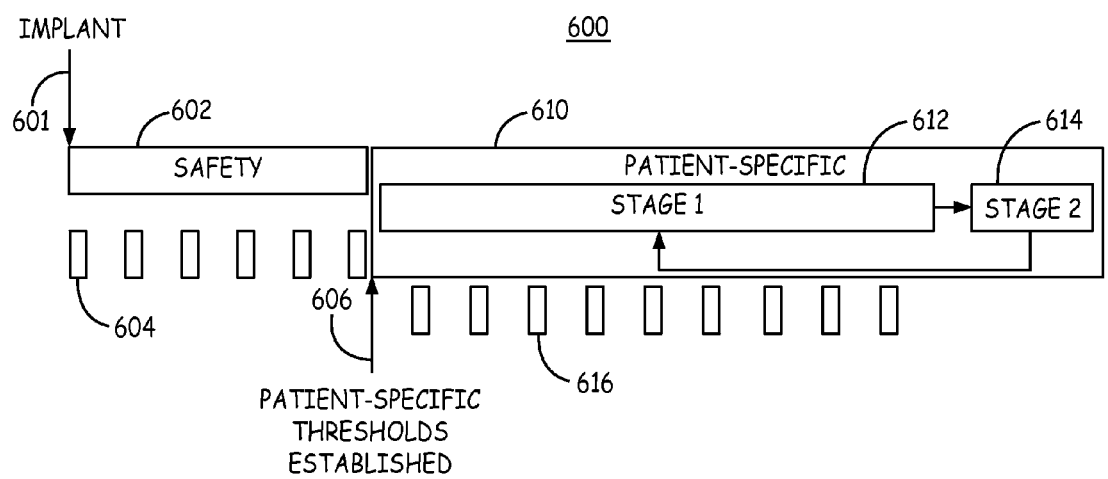
FIG. 8 is a time line of a tachyarrhythmia detection process according to an illustrative embodiment.

FIG. 8 is a time line 600 of a tachyarrhythmia detection technique according to an illustrative embodiment. Upon implantation at 601, the IMD immediately and enters the initial safety detection process 602 which relies on population-based detection thresholds. The initial safety detection process 602 may be started automatically upon detecting an implant condition, e.g. based on electrical impedance measurements. Alternatively, a clinician may enable the safety detection process 602, for example by transmitting a single command or activating a magnetic switch. In one embodiment, population-based detection thresholds are used exclusively and applied to rate-based and/or gross morphology features determined from n-second EGM segments. Accordingly, the IMD operates immediately for detecting potentially lethal tachyarrhythmia without user-programming of a single detection parameter in one embodiment.

During the initial safety detection process 602, learning windows 604 are automatically set and confirmed periodically by the IMD during which patient-specific ECG signal features are determined. The features determined during each learning window 604 are accumulated over multiple windows and used to determine ECG signal feature values used for setting patient-specific detection thresholds. In one embodiment, the patient-specific feature values are beat feature values determined from cardiac cycles and are representative of the feature during non-shockable cardiac cycles, e.g. NSR cycles, in the learning window. In other embodiments, the patient-specific features include gross signal features determined from n-second segments. In still other embodiments, patient-specific features include features determined from the ECG signal during both NSR and confirmed shockable rhythms.

When patient-specific features have been determined for a required number of learning windows 604, patient-specific detection thresholds are established at time 606. Upon establishing the patient-specific detection thresholds, the detection process is switched from the population-based safety detection process to a patient-specific detection process 610. The patient specific detection process 610 includes detection criteria requiring determination of signal features for which patient-specific thresholds were established at the end of the safety mode. At least one of these signal features is not used for detecting a shockable rhythm during the initial safety detection process 602. As such, the switch to the patient-specific detection process is more than a mere substitution of patient-specific thresholds for the initial population-based thresholds; different signal feature determinations and different criteria than that used during the initial safety detection process 602 are used for detecting and discriminating rhythms during patient-specific process 610.

Patient specific process 610 includes a first stage 612 analyzing a subset of the signal features for which patient-specific thresholds have been established. The first stage is less processing intensive than the second stage 614 and may therefore require less battery current potentially improving device longevity. The first stage 612 operates to detect a concerning rhythm. Updates to patient-specific thresholds may be made during the first stage 612 as new feature values are determined during confirmed learning windows 616 when a concerning rhythm is not being detected.

If a concerning rhythm is detected during the first stage 612, the detection process 610 transitions to the second stage 614 to perform a higher level analysis of signal features, which may include both beat features and gross morphology features. The second stage may use all available patient-specific thresholds. The second stage may additionally use population-based thresholds applied to gross morphology features and/or additional sensor signals. Learning windows 616 will not be set during the second stage in some embodiments. Patient-specific thresholds are updated only in response to learning windows during confirmed non-shockable rhythms. In other embodiments, feature values may be determined during learning windows set during a concerning rhythm, second stage operation, and used to set patient-specific feature values indicative of a shockable rhythm when the second stage analysis results in a shockable rhythm detection. Shockable rhythm feature values may be used in combination with non-shockable rhythm feature values for setting patient-specific detection thresholds.

The second stage 614 may be terminated upon therapy delivery or upon detecting a non-shockable rhythm. The patient-specific rhythm detection process 610 returns to the first stage 612 and may adjust detection thresholds as described previously based on confidence zones of beat feature analysis outcomes and gross morphology analysis outcomes.

The detection processes represented by timeline 600 may operate without programming of detection parameters. The population-based initial safety detection mode 602 starts automatically and is switched off automatically upon establishing patient-specific thresholds at 606. The population-based initial safety detection process 602 and learning period during which learning windows 604 are set may operate for a few minutes up to several days or weeks depending on the patient's rhythm and the patient-specific thresholds required for the patient-specific detection process 610. The patient-specific detection process 610 may continue to evolve over time to improve or update patient-specific thresholds as changes occur in the ECG signal and the patient's underlying rhythm. Accordingly, user programming of detection parameters may never be required. In some embodiments, user verification of detected rhythms is provided as feedback to the IMD for verifying patient-specific threshold values. In some embodiments, rate or interval based detection parameters may be programmed by a user, such as interval zones and NID, for use during the initial safety detection process 602, but all other detection parameters relating to gross morphology and beat features are either pre-set population values or automatically determined patient specific values.

Thus, a method and apparatus for performing tachyarrhythmia detection have been presented in the foregoing description with reference to specific embodiments. For example, various methods described herein may include steps performed in a different order or combination than the illustrative examples shown and described herein. It is appreciated that various modifications to the referenced embodiments may be made without departing from the scope of the disclosure as set forth in the following claims.

The invention claimed is:

1. A medical device for detecting and treating tachyarrhythmia, comprising:
a sensing module configured to sense cardiac events in response to a cardiac signal acquired via at least some of a plurality of electrodes; and
a processing module configured to:
perform an initial detection process comprising detecting a shockable cardiac rhythm by comparing the cardiac signal to a first set of detection criteria;
establish, by analyzing the cardiac signal, at least one patient-specific detection threshold during the initial detection process; and
upon establishing the at least one patient-specific detection threshold, stop the initial detection process and start a next detection process comprising comparing the cardiac signal to a second set of detection criteria comprising the at least one patient-specific detection threshold,
the first set of detection criteria relating to a first set of cardiac signal features, and the second set of detection criteria relating to a second set of cardiac signal features different than the first set of cardiac signal features.

2. The device of claim 1, wherein the first set of detection criteria comprises only population-based detection thresholds.

3. The device of claim 1, wherein comparing the cardiac signal to a first set of detection criteria comprises determining a gross morphology feature of the cardiac signal over a predetermined time interval independent of a timing of a cardiac cycle.

4. The device of claim 1, wherein establishing the at least one patient-specific detection threshold comprises determining a beat feature of the cardiac signal representative of a cardiac cycle.

5. The device of claim 1, wherein the processing module is further configured to determine a beat feature of a cardiac cycle of the cardiac signal during the next detection process that is not determined during the initial detection process and compare the beat feature to one of the patient-specific detection thresholds.

6. The device of claim 1, wherein the processing module is further configured to:
detect a concerning cardiac rhythm during a first stage of the next detection process; and
discriminate the concerning cardiac rhythm as one of a shockable rhythm and a non-shockable rhythm during a second stage of the next detection process.

7. The device of claim 6, wherein the processing module is further configured to update the at least one patient-specific detection threshold during the first stage when a concerning cardiac rhythm is not being detected.

8. The device of claim 6, wherein the processing module is configured to discriminate the concerning cardiac rhythm by:
determining a cardiac cycle feature and in a first comparison compare the cardiac cycle feature to one of the patient-specific thresholds; and
determining a gross morphology feature across a cardiac signal segment and in a second comparison compare the gross morphology feature to a population-based threshold.

9. The device of claim 8, wherein the processing module is further configured to:
rate a first confidence of the first comparison;
rate a second confidence of the second comparison; and
adjust one of the patient-specific threshold and the population-based threshold in response to comparing the first confidence and the second confidence ratings.

10. The device of claim 1, wherein the processing module is configured to establish the patient specific threshold by:
setting a learning window;
confirming the learning window corresponds to a non-shockable rhythm using a non-ECG signal;
determining a feature of the cardiac signal for multiple cardiac cycles during the learning window; and
setting the patient-specific threshold in response to the feature.

11. The device of claim 1, wherein the processing module is configured to:
set a learning window;
determine a feature of the cardiac signal for multiple cardiac cycles during the learning window;
set the patient-specific threshold in response to the feature; and
select at least one of a sensing vector and a decay rate of a sensing threshold in response to the feature.

12. The device of claim 1, wherein the processing module is configured to:
set a learning window;
determine a similarity between cycles of the cardiac signal over the learning window;
determine a feature of the cardiac signal for multiple cardiac cycles during the learning window if the similarity meets a correlation requirement; and
set the patient-specific threshold in response to the feature.

13. The device of claim 1, wherein the processing module is configured to:
determine a feature of the cardiac signal;
compare the feature to a historic value of the feature;
update the historic value of the feature if the determined feature is within a range of the historic value; and
set the patient-specific threshold in response to the updated historic value,
the range being adjusted to a relatively narrower range as the historic value is updated over time.

14. The device of claim 1, wherein the processing module is configured to perform the initial detection process and the next detection process without a user-programmed detection parameter.

15. The device of claim 1, further comprising the plurality of electrodes.

16. The device of claim 15, further comprising:
a signal generator module configured to deliver a shock therapy via at least some of the plurality of electrodes,
wherein the processing module is configured to control the signal generator module to deliver the shock therapy in response to detection of ventricular tachycardia or ventricular fibrillation.

17. A medical device for detecting and treating tachyarrhythmia, comprising:

means for sensing cardiac events in response to a cardiac signal acquired via at least some of a plurality of electrodes;

means for performing an initial detection process comprising detecting a shockable cardiac rhythm by comparing the cardiac signal to a first set of detection criteria;

means for establishing, by analyzing the cardiac signal, at least one patient-specific detection threshold during the initial detection process; and means for, upon establishing the at least one patient-specific detection threshold, stopping the initial detection process and starting a next detection process comprising comparing the cardiac signal to a second set of detection criteria comprising the at least one patient-specific detection threshold, the first set of detection criteria relating to a first set of cardiac signal features, and the second set of detection criteria relating to a second set of cardiac signal features different than the first set of cardiac signal features.

18. The device of claim 17, wherein the first set of detection criteria comprises only population-based detection thresholds.

19. The device of claim 17, wherein comparing the cardiac signal to a first set of detection criteria comprises determining a gross morphology feature of the cardiac signal over a predetermined time interval independent of a timing of a cardiac cycle.

20. The device of claim 17, wherein the means for establishing the at least one patient-specific detection threshold comprises means for determining a beat feature of the cardiac signal representative of a cardiac cycle.

21. The device of claim 17, further comprising means for determining a beat feature of a cardiac cycle of the cardiac signal during the next detection process that is not determined during the initial detection process and comparing the beat feature to one of the patient-specific detection thresholds.

22. The device of claim 17, further comprising:
means for detecting a concerning cardiac rhythm during a first stage of the next detection process; and
means for discriminating the concerning cardiac rhythm as one of a shockable rhythm and a non-shockable rhythm during a second stage of the next detection process.

23. The device of claim 22, further comprising means for updating the at least one patient-specific detection threshold during the first stage when a concerning cardiac rhythm is not being detected.

24. The device of claim 22, wherein the means for discriminating the concerning cardiac rhythm comprises:
means for determining a cardiac cycle feature and in a first comparison compare the cardiac cycle feature to one of the patient-specific thresholds; and
means for determining a gross morphology feature across a cardiac signal segment and in a second comparison compare the gross morphology feature to a population-based threshold.

25. The device of claim 24, further comprising:
means for rating a first confidence of the first comparison;
means for rating a second confidence of the second comparison; and
means for adjusting one of the patient-specific threshold and the population-based threshold in response to comparing the first confidence and the second confidence ratings.

26. The device of claim 17, wherein the means for establishing the patient specific threshold comprises:
means for setting a learning window;
means for confirming the learning window corresponds to a non-shockable rhythm using a non-ECG signal;
means for determining a feature of the cardiac signal for multiple cardiac cycles during the learning window; and
means for setting the patient-specific threshold in response to the feature.

27. The device of claim 17, further comprising:
means for setting a learning window;
means for determining a feature of the cardiac signal for multiple cardiac cycles during the learning window;
means for setting the patient-specific threshold in response to the feature; and
means for selecting at least one of a sensing vector and a decay rate of a sensing threshold in response to the feature.

28. The device of claim 17, further comprising:
means for setting a learning window;
means for determining a similarity between cycles of the cardiac signal over the learning window;
means for determining a feature of the cardiac signal for multiple cardiac cycles during the learning window if the similarity meets a correlation requirement; and
means for setting the patient-specific threshold in response to the feature.

29. The device of claim 17, further comprising:
means for determining a feature of the cardiac signal;
means for comparing the feature to a historic value of the feature;
means for updating the historic value of the feature if the determined feature is within a range of the historic value; and
means for setting the patient-specific threshold in response to the updated historic value,
the range being adjusted to a relatively narrower range as the historic value is updated over time.

30. The device of claim 17, further comprising means for performing the initial detection process and the next detection process without a user-programmed detection parameter.

31. The device of claim 17, further comprising the plurality of electrodes.

32. The device of claim 31, further comprising means for delivering a shock therapy via at least some of the plurality of electrodes in response to detection of ventricular tachycardia or ventricular fibrillation.

33. A medical device for detecting and treating tachyarrhythmia, comprising:
a sensing module configured to sense cardiac events in response to a cardiac signal acquired via at least some of a plurality of electrodes; and
a processing module configured to:
perform an initial detection process comprising detecting a shockable cardiac rhythm by comparing the cardiac signal to a first set of detection criteria comprising population-based detection thresholds, wherein the initial detection process is performed without a user-programmed detection parameter;
establish, by analyzing the cardiac signal, at least one patient-specific detection threshold during the initial detection process; and
upon establishing the at least one patient-specific detection threshold, stop the initial detection process and start a next detection process comprising comparing the cardiac signal to a second set of detection criteria comprising the at least one patient-specific detection threshold, wherein the next detection process is performed without a user-programmed detection parameter, the first set of detection criteria relating to a first set of cardiac signal features, and the second set of detection criteria relating to a second set of cardiac signal features different than the first set of cardiac signal features.

34. The device of claim 33, further comprising the plurality of electrodes.

35. The device of claim 34, further comprising:
a signal generator module configured to deliver a shock therapy via at least some of the plurality of electrodes,
wherein the processing module is configured to control the signal generator module to deliver the shock therapy in response to detection of ventricular tachycardia or ventricular fibrillation.

36. The device of claim 1, wherein the processing module is configured to perform the initial detection process without the patient-specific detection threshold being used by the initial detection process.

37. The device of claim 1, wherein the initial detection process comprises detecting the shockable cardiac rhythm by comparing a first portion of the cardiac signal to the first set of detection criteria, and the next detection process comprises comparing a second portion of the cardiac signal to the second set of detection criteria comprising the at least one patient-specific detection threshold, the second portion of the cardiac signal being different from the first portion of the cardiac signal.

38. The device of claim 17, wherein the means for performing the initial detection process comprises means for performing the initial detection process without the patient-specific detection threshold being used by the initial detection process.

39. The device of claim 17, wherein the initial detection process comprises detecting the shockable cardiac rhythm by comparing a first portion of the cardiac signal to the first set of detection criteria, and the next detection process comprises comparing a second portion of the cardiac signal to the second set of detection criteria comprising the at least one patient-specific detection threshold, the second portion of the cardiac signal being different from the first portion of the cardiac signal.

40. The device of claim 33, wherein the processing module is configured to perform the initial detection process without the patient-specific detection threshold being used by the initial detection process.

41. The device of claim 33, wherein the initial detection process comprises detecting the shockable cardiac rhythm by comparing a first portion of the cardiac signal to the first set of detection criteria, and the next detection process comprises comparing a second portion of the cardiac signal to the second set of detection criteria comprising the at least one patient-specific detection threshold, the second portion of the cardiac signal being different from the first portion of the cardiac signal.

* * * * *